(12) United States Patent
Hartog

(10) Patent No.: US 8,989,526 B2
(45) Date of Patent: Mar. 24, 2015

(54) RAMAN AMPLIFICATION IN DISTRIBUTED OPTICAL FIBER SENSING SYSTEMS

(75) Inventor: Arthur H. Hartog, Winchester (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 1071 days.

(21) Appl. No.: 12/375,306

(22) PCT Filed: Jul. 12, 2007

(86) PCT No.: PCT/GB2007/002606
§ 371 (c)(1),
(2), (4) Date: May 4, 2009

(87) PCT Pub. No.: WO2008/012498
PCT Pub. Date: Jan. 31, 2008

(65) Prior Publication Data
US 2009/0263069 A1    Oct. 22, 2009

(30) Foreign Application Priority Data

Jul. 28, 2006 (GB) .................................. 0614991.8
Feb. 9, 2007 (GB) .................................. 0702535.6

(51) Int. Cl.
G02B 6/00 (2006.01)
G01D 5/353 (2006.01)
G01M 11/00 (2006.01)
G01N 21/63 (2006.01)

(52) U.S. Cl.
CPC ............. *G01D 5/353* (2013.01); *G01M 11/319* (2013.01); *G01N 2021/638* (2013.01)
USPC ........................................................... 385/12

(58) Field of Classification Search
CPC .... G01L 1/242; G01L 1/246; G01N 21/7702; G02B 6/00
USPC ........................................................... 385/12
See application file for complete search history.

(56) References Cited

U.S. PATENT DOCUMENTS

2004/0042061 A1* 3/2004 Islam et al. .................... 359/334
2005/0117830 A1* 6/2005 Hartog et al. .................... 385/12

FOREIGN PATENT DOCUMENTS

GB          2182222 A  *  5/1987
WO    WO 2006/003206 A  *  1/2006

OTHER PUBLICATIONS

Lees et al. "OTDR system using Raman amplification of a 1.65 micron probe pulse", Jun. 5, 1997, Electronics Letters, vol. 33, No. 12. pp. 1080-1081.*
Kee et al. "Distributed optical fibre sensing at 1.65 micron using a Q-switched fibre laser", May 22, 2000, Proceedings of the SPIE, vol. 4074, pp. 283-284.*
Kee et al. "Extended range optical time domain reflectometry system at 1.65 micron based on delayed Raman amplification" Mar. 1, 1998, Optics Letters, vol. 23, No. 5, pp. 349-351.*

* cited by examiner

*Primary Examiner* — Mark Robinson
*Assistant Examiner* — Erin Chiem (57) ABSTRACT

A method of providing Raman amplification in an optical fiber sensing system, comprises generating a probe pulse of light and launching the pulse into a sensing optical fiber, generating pump light at a shorter wavelength and modulating it to produce a time-varying intensity profile, and launching the pump light into the sensing fiber. such that the intensity of the launched pump light during launch of the probe pulse is different from the intensity at other times. Raman amplification of backscattered light produced by the probe pulse as it propagates along the fiber is achieved, as is amplification of the probe pulse if the pump power is non-zero during launch of the probe pulse.

21 Claims, 7 Drawing Sheets

RAMAN AMPLIFICATION IN DISTRIBUTED OPTICAL FIBER SENSING SYSTEMS

BACKGROUND OF THE INVENTION

1. Field of the Invention

The present invention relates to improvements in the use of Raman amplification in distributed optical fiber sensing systems, such as optical time domain resolution systems.

2. Description of Related Art

There is an interest in extending the range of distributed optical fiber sensors, in which backscattered light produced by a propagating probe pulse is collected to yield measurements of parameters associated with the fiber. Of particular interest are systems based on Brillouin and/or Rayleigh backscatter. A recent system [1] proposed a combination of distributed Raman amplification over the first 50 km of a sensing fiber and discrete erbium doped fiber amplifiers at 50 and 75 km, and was demonstrated to achieve 100 km range in the case of the determination of the Brillouin frequency shift with a resolution of well below 1 MHz (equivalent to better than 1 K resolution). To achieve this, continuous-wave pump power (460 mW) was co-propagated with the probe pulse, thus resulting in Raman gain for the probe pulse and also for any backscatter power falling within the gain bandwidth of the Raman process. However, it was found necessary to reduce the probe pulse power in order to prevent the undesirable non-linear effects that occur when a probe pulse exceeds a certain power level. As a result, the point within the system where the performance was worst was nearest to the acquisition equipment. Clearly, the gains could be balanced more effectively, but a fundamental problem with such a system is that the gain for the probe pulse cannot be adjusted independently of that for the backscatter. In addition, the gain experienced by the probe pulse depletes the pump power locally, which means that the probe pulse is amplified when it is strongest, and then when its intensity has decayed there is no more pump power available to amplify it.

Earlier work using Raman amplification [2, 3] did not co-propagate the pump power from the interrogation equipment so the problems discussed above did not arise. An alternative system uses remotely-pumped fiber amplifiers [4]. Attempts to control the Raman gain have been made [5, 6], using pulsed Raman amplification such that Raman gain for the probe pulse occurs only some distance along the fiber. By timing the launch of a pump pulse and a probe pulse, the position at which they overlap can be controlled owing to the difference in their propagation velocities. In this way, the probe pulse can be allowed to decay somewhat before being amplified by transfer of energy from the pump pulse, to limit nonlinear effects. A drawback of this approach, however, is that the probe pulse is not amplified uniformly since one of its edges overlaps with the pump pulse before the remainder of the probe pulse and thus this edge receives all the amplification. As a result, distortion of the probe pulse may result which in turn might cause non-linear effects, notably self-phase modulation. In addition, this approach does not allow the returning backscattered light to be amplified at the same time, because the probe power is confined to the duration of the probe pulse.

BRIEF SUMMARY OF THE INVENTION

Accordingly, a first aspect of the present invention is directed to a method of providing Raman amplification in an optical fiber sensing system, comprising: generating a probe pulse of light at a probe wavelength; launching the probe pulse into a sensing optical fiber; generating pump light at a pump wavelength shorter than the probe wavelength; modulating the pump light to produce a time-varying intensity profile; launching the pump light into the sensing fiber such that the intensity of the launched pump light during launch of the probe pulse is different from the intensity at one or more other times; and propagating the pump light and the probe pulse along the sensing fiber to achieve Raman amplification of backscattered light produced by the probe pulse as it propagates.

Hence, the pump power is modulated such that the pump power travelling at about the same time as the probe pulse (allowing for chromatic dispersion effects, where different wavelengths have different propagation velocities in the fiber) is different from the pump power travelling in the fiber at other times, and in particular when the backscattered light is travelling back along the fiber. In this way, the Raman amplification experienced by the probe pulse and by the backscatter can be controlled separately, to optimise the performance of the system. The backscattered light can be amplified to give a bigger output signal from the fiber, thus improving the signal-to-noise ratio, while amplification experienced by the probe pulse (which gives a corresponding increase to the backscatter power so can be beneficial) can be limited to keep the probe pulse below the power threshold for nonlinear distortion effects.

In some embodiments, the intensity of the pump light during launch of the probe pulse is substantially zero so that the probe pulse experiences substantially no Raman amplification. This arrangement allows the maximum probe pulse power that tolerates nonlinear effects to be used at launch, so that high backscatter levels are received from the front part of the fiber, while backscatter produced at all points along the fiber is amplified as it propagates back along the fiber and meets the oncoming pump power.

Alternatively, the intensity of the pump light during launch of the probe pulse may be greater than zero, so that the probe pulse experiences some Raman amplification. While the initial probe pulse power should be reduced so that the Raman amplification does not push it above the nonlinear threshold, thus also reducing the initial backscatter power, the probe pulse power can be maintained at a higher level over a longer distance than with a zero pump power at probe launch. Backscatter levels are thus higher over more of the fiber, thereby extending the range of the system. Preferably, the intensity of the pump light during the launch of the probe pulse is sufficient to amplify the probe pulse to an intensity below a threshold above which the probe pulse would be distorted by nonlinear effects, so that the benefits of an extended range are not offset by a degradation in signal quality resulting from nonlinear distortion.

The method may further comprise introducing a time delay into forward propagating light in the sensing fiber at either the probe wavelength or the pump wavelength such that after the delay, the probe pulse overlaps a part of the intensity profile of the pump light having a greater intensity than the part overlapped by the probe pulse before the delay, and experiences Raman amplification. The time delay can be introduced at any location along the sensing fiber, so that the probe pulse can begin to experience Raman amplification at a selected point, such as that where the probe power has decayed sufficiently that nonlinear effects will not become a problem if the pulse is amplified. Thus, the time delay may be introduced such that the intensities of the probe pulse and of the pump light with which it overlaps after the delay are such that the probe pulse is amplified by the pump light to an intensity below a threshold above which the probe pulse would be distorted by nonlinear effects. The probe pulse can thereby be maintained near a maximum power level that avoids distortion over some considerable distance, particularly if several time delays are introduced so that the pump power available to amplify the probe pulse is repeatedly boosted. Also, in the case of a non-zero pump power at probe launch, the pump energy that has been depleted by conversion to the probe wavelength during Raman amplification can be replenished by the time shift, to maintain probe amplification.

The invention thus offers various improvements to Raman amplification of the various wavelengths propagating in a sensing fiber. By starting with high probe pulse power and a moderate (or zero) pump power at the launching end of the fiber, the near-end backscatter signals can be made strong due to a strong probe and yet amplification of the backscatter signals can still be maximised. Further along the fiber, the amplified backscatter signals are reduced because of the losses experienced by the probe and also a reduction of the Raman gain, since the pump is also attenuated by propagation losses. Introducing a relative delay between the modulated pump and the probe pulse allows the probe pulse to be switched from a low power to a high power region of the pump waveform, to increase Raman amplification. This also allows the depleted power that travels with the probe pulse to be replenished.

The method may further comprise passing forward propagating light in the sensing fiber through one or more rare earth-doped optical fiber amplifiers integrated into the sensing fiber to amplify the intensity of the light. Discrete fiber amplifiers can be used to provide gain once the Raman amplification is no longer sustainable owing to depletion of the pump power from both conversion to the probe and backscatter wavelengths and propagation losses in the fiber.

Also, the method may further comprise: collecting backscattered light returned from the sensing fiber; and processing the collected backscattered light to determine information about the sensing fiber and/or an environment in which it is deployed.

A second aspect of the present invention is directed to an optical fiber sensing system for providing Raman amplification, comprising: a sensing optical fiber deployable in a sensing environment; a first optical source operable to generate probe pulses of light at a probe wavelength; a second optical source operable to generate pump light at a pump wavelength shorter than the probe wavelength; means operable to modulate the pump light generated by the second optical source to produce a time-varying intensity profile; and an optical coupling device arranged to receive the probe pulses from the first optical source and modulated pump light from the modulation means and to launch the probe pulses and the pump light into the sensing fiber for propagation along the sensing fiber to achieve Raman amplification of backscattered light produced by the probe pulses as they propagate, such that the intensity of the launched pump light during launch of the probe pulses is different from the intensity at one or more other times. The intensity of the pump light during launch of the probe pulse may be substantially zero so that the probe pulse experiences substantially no Raman amplification, or the intensity of the pump light during launch of the probe pulse may be greater than zero so that the probe pulse experiences some Raman amplification. For example, the intensity of the pump light during the launch of the probe pulse may be sufficient to amplify the probe pulse to an intensity below a threshold above which the probe pulse would be distorted by nonlinear effects.

The system may further comprise an optical time delay device integrated into the sensing fiber and operable to introduce a time delay into forward propagating light in the sensing fiber at either the probe wavelength or the pump wavelength such that after the delay, the probe pulse overlaps a part of the intensity profile of the pump light having a greater intensity than the part overlapped by the probe pulse before the delay, and experiences Raman amplification. The optical time delay device may be located such that the intensities of the probe pulse and of the pump light with which it overlaps after the delay are such that the probe pulse is amplified by the pump light to an intensity below a threshold above which the probe pulse would be distorted by nonlinear effects. The optical time delay device may comprise an optical fiber delay line coupled at both ends to the sensing fiber by a wavelength division multiplexer arrangement configured to pass light at one of the pump wavelength and the probe wavelength directly along the sensing fiber and to direct light at the other of the pump wavelength and the probe wavelength along the optical delay line before directing it further along the sensing fiber.

The system may further comprise one or more rare-earth optical fiber amplifiers integrated into the sensing fiber and operable to amplify the intensity of forward propagating light in the sensing fiber. Also, the system may further comprise: an optical detector for collecting backscattered light returned from the sensing fiber; and a processor operable to process one or more signals output from the optical detector to determine information about the sensing fiber and/or an environment in which it is deployed.

BRIEF DESCRIPTION OF THE DRAWINGS

For a better understanding of the invention and to show how the same may be carried into effect, reference is now made by way of example to the accompanying drawings in which.

DETAILED DESCRIPTION OF THE INVENTION

Figure 1:
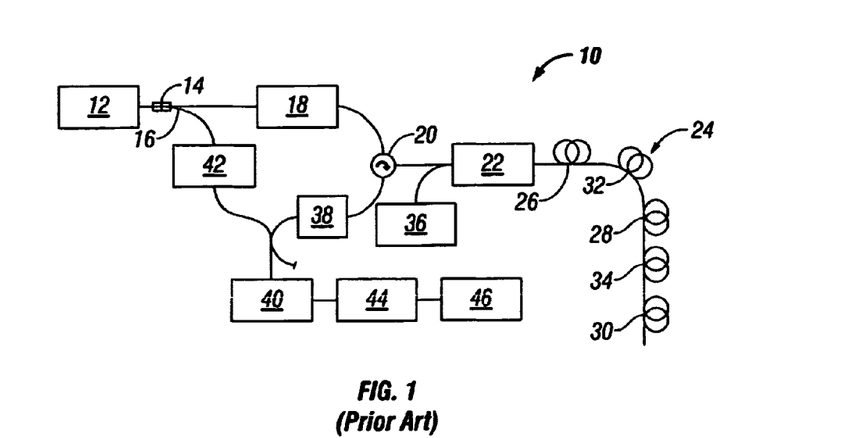
FIG. 1 shows a schematic diagram of an optical time domain reflectometer system according to the prior art.

FIG. 1 shows a schematic diagram of a known optical time domain reflectometer system [1] intended to measure Brillouin backscattered light arising from the propagation along a deployed optical fiber of a probe pulse launched into the fiber. Similar systems can measure Raman backscattering (Stokes and anti-Stokes light) and/or direct backscatter at the wavelength of the probe pulse. The system 10 comprises an optical source 12, such as a continuous-wave narrowband laser operating at 1550 nm, the output of which is passed through an isolator 14 (optional) before being divided between two branches by a splitter 16. Light in a first branch enters a pulse amplifier module 18 which amplifies and modulates the light to produce probe pulses, which may have a duration of about 100 ns, for example. Each probe pulse leaves the pulse amplifier module 18 and enters a first port of an optical circulator 20, the second port of which launches the pulses (via a polarisation scrambler 22) into a sensing fiber 24 that is deployed in a region of interest. The sensing fiber 24 comprises a first length of fiber 26 of 50 km, a second length of fiber 28 of 25 km, and a third length of fiber 30 of 25 km. First and second erbium-doped fiber amplifiers (EDFA) 32, 34 are respectively positioned between the first length of fiber 26 and the second length of fiber 28, and between the second length of fiber 28 and the third length of fiber 30.

A second optical source 36 produces continuous-wave light at a pump wavelength of 1480 nm (shorter than the probe wavelength so that Raman amplification can occur in the sensing fiber 24). The pump light is also launched in the sensing fiber 24 via the polarisation scrambler 22; a wavelength division multiplexer (not shown) combines the probe pulses and the pump light.

Backscattered light produced within the sensing fiber 24 returns to the launch end of the fiber 24, and passes through the polarisation scrambler 22 to the second port of the optical circulator 20, where it is passed to the third port of the circulator 20 and delivered to an amplified spontaneous emission (ASE) filter 38, designed to filter out as much as possible of the amplified spontaneous emission from the optical amplification processes in the sensing fiber 24. After filtering, the backscattered light passes to an optical detector and receiver 40. In this particular system, light at the probe wavelength from the first optical source 12 that enters a second branch from the splitter 16 is passed through a polarisation scrambler 42 and is then coupled to the optical detector and receiver 40 so as to mix on the detector with the backscattered light. A microwave module 44 selects a particular frequency band within the electrical output of the optical detector and receiver 40 and amplifies and detects (rectifies) this selected band. This particular arrangement, known as coherent, or heterodyne, detection, is just one way of separating the Brillouin backscatter from the total backscatter spectrum. An optical filtering arrangement may be used instead, for example. The output of the microwave module 44 is delivered to further equipment 46, such as an oscilloscope (for display of the output) or a processor operable to process the backscatter signal to determine parameters relating to the sensing fiber 24 and its environment, such as temperature, strain, or attenuation.

In the system of FIG. 1, the co-propagating pump light amplifies the probe pulse as it travels down the first length 26 of the sensing fiber 24 by the action of Raman amplification. Hence the first fiber length 26 acts as a distributed Raman amplifier. Amplification of the probe pulse compensates for the inherent attenuation of the probe pulse as it propagates, so that more light is available for Brillouin shifting and backscattering, giving a larger backscattered signal. In addition, the pump light is available to amplify the returning backscatter, because the pump light is a continuous-wave emission so is present throughout the fiber at all times. This also boosts the backscattered signal and compensates for propagation losses. One benefit of the Raman amplification process is that the backscattered light is amplified immediately as it is produced, rather than after propagation back to an optical amplifier, so the effect of the fiber loss (attenuation) is reduced. However, Raman amplification occurs only with relatively high pump powers. In a typical fiber, about 80 mW of pump power is required just to overcome the fiber losses. Since the pump light itself is subject to propagation losses, this process is rather difficult to control. Too much pump power amplifies the probe pulse to a point where undesirable non-linear effects occur, and too little pump power offers only minor amplification benefits. For lower powers, discrete optical fiber amplification can be effected using short sections of rare earth-doped fiber, for example erbium-doped fiber. In the system of FIG. 1, the two approaches are combined, by interspersing the lengths of sensing fiber 26, 28, 30 with EDFAs 32, 34. However, in this system, it was found necessary to reduce the power of the probe pulse in order to avoid non-linear effects.

Figure 2:
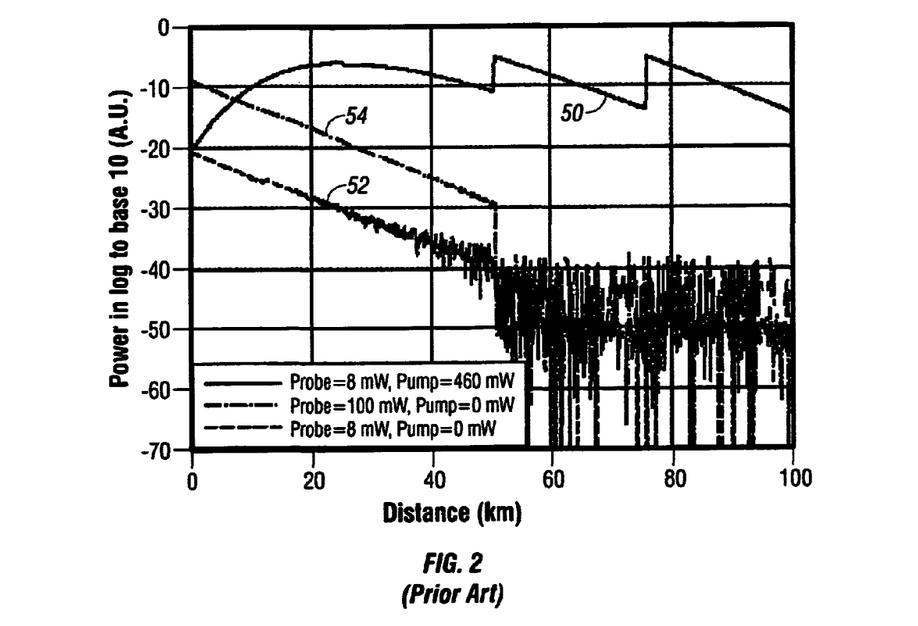
FIG. 2 shows plots of Brillouin backscatter signals measured with the prior art system of FIG. 1.

FIG. 2 shows plots of Brillouin backscattered light recorded from the fiber 24 in the system of FIG. 1, shown as the distribution of power with distance along the fiber. Curve 50 shows the result of propagating 0.46 W of pump power with a probe pulse power of 8 mW. Curve 52 shows the result obtained for the same probe pulse power but without pump power (hence no Raman amplification), and curve 54 is the result also without pump power but with the probe pulse power increased to 100 mW.

It is not possible from the curve 50 of FIG. 2 to deduce in the increase of backscatter power over the first 50 km section of fiber 26 (before the first EDFA 32) what is the contribution of the Raman gain for the probe pulse and what is due to Raman gain experienced by the backscatter signal. However, it can be seen that the signal is below that for the unamplified but higher probe pulse power (curve 54) over approximately the first 8 km of the sensing fiber. Hence the pump power and resulting Raman gain produce an initial penalty in performance.

Figure 3:
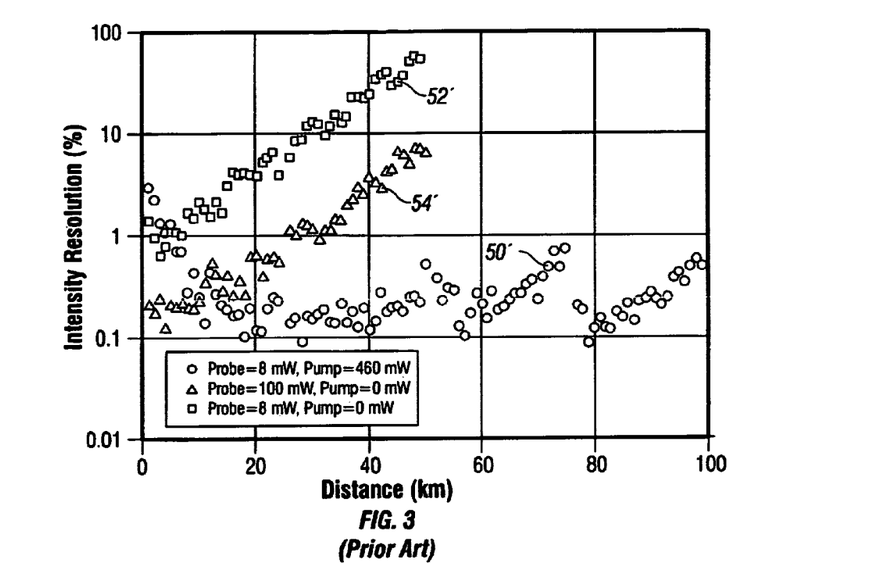
FIG. 3 shows plots of the resolution of Brillouin backscatter signals measured with the prior art system of FIG. 1.

FIG. 3 illustrates the effects of this penalty. Shown are plots of the achieved intensity resolution of the backscatter as a function of distance along the fiber for the three curves of FIG. 2, with the corresponding data indicated by the same reference numerals with primes. These data indicate that when the pump light is used, the system performance is worse (highest percentage resolution) than for no pump light over the first few kilometres of the fiber. This is a direct result of having to reduce the probe power to avoid amplification to above the threshold for nonlinear effects, and is worse in the first section of fiber than when the pump was turned off and the probe power increased to 100 mW. It would be possible to perform measurements under both conditions to achieve an overall acceptable result, but this would require additional measurement time and is hence unattractive.

For the purposes of demonstrating the improvements in performance that can be obtained using embodiments of the present invention, the conditions of the Raman amplified measurement made using the prior art system of FIG. 1 have been modelled so that comparison can be made with embodiments of the invention. The modelling allows the gain for the probe and the gain for the Brillouin backscatter to be considered independently.

Figure 4:
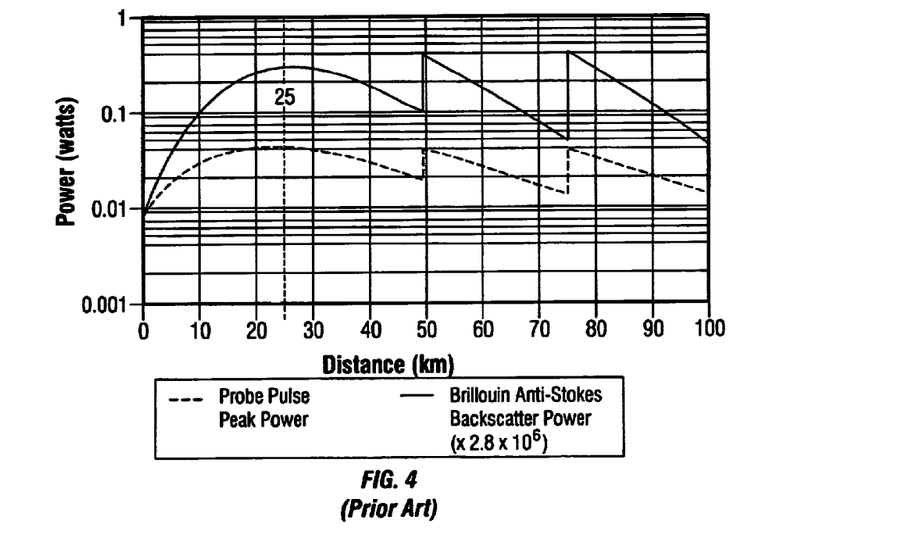
FIG. 4 shows plots of modelled intensities of Brillouin backscatter and of a probe pulse under the conditions of the prior art system of FIG. 1.

FIG. 4 shows the results of the modelling of the system of FIG. 1. The solid line shows the power of the Brillouin anti-Stokes backscatter as distributed over the length of the fiber, and the dashed line shows the power of the probe pulse, also distributed over the length of the fiber. The probe pulse grows by a factor of 5 (from 8 to 40 mW), i.e. 7 dB over the initial 25 km of the sensing fiber, despite the fiber attenuation that can be estimated at about 5 dB. Thus there is a net power gain for the probe pulse of a factor of 15. The backscatter gain is a factor of 7.5 in addition to the fiber attenuation, i.e. an overall power gain of about 22. The rises in the curves at 50 km and 75 km are due to the two EDFAs. In FIG. 4, the backscattered power has been scaled to match the probe power at the launching point in order to simplify power comparisons. In this case, the pump power was set to 400 mW in order to match the experimental results with the model. This power level is 15 percent lower than in the prior art publication [1]; this is justified by possible losses in the multiplexing and the accuracy to which the fiber parameters are known.

The present invention proposes techniques for improving the performance of optical fiber sensing systems that use Raman amplification, such as that of FIG. 1. It is proposed that the power of the pump light launched into the sensing fiber be varied as a function of time. According to various embodiments, this allows the Raman gain experienced by the probe pulse and the Raman gain experienced by the backscattered light (both provided by the pump light) to be separately controlled, or for the Raman gain to be confined to the backscatter, if desired.

Figure 5:
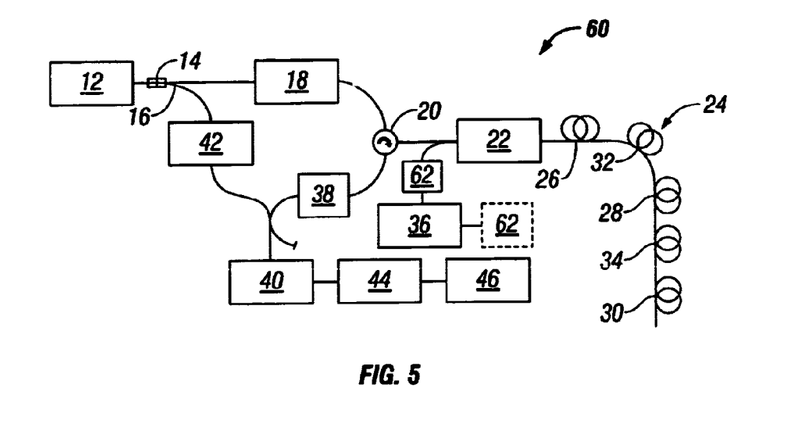
FIG. 5 shows a schematic diagram of an optical time domain reflectometer system according to an embodiment of the present invention.

FIG. 5 shows a schematic diagram of an optical fiber sensing system 60 similar to that of FIG. 1, but which includes modification in accordance with the present invention. The system 60 comprises the same components as the system 10 of FIG. 1, and additionally includes an optical modulator 62, whose purpose is to modulate the intensity of the pump light generated by the second optical source 36 to give it a time-varying intensity profile, i.e. the intensity of the pump light is non-constant. The optical modulator 62 can be arranged to receive the output from the second optical source 36 and apply the appropriate modulation, as indicated in FIG. 5 by the solid box labelled 62. Alternatively, the modulator 62 can control the function of the second optical source 36 so that the time-varying pump light is generated directly, as indicated in FIG. 5 by the phantom box 62.

The time-varying intensity profile of the pump light is configured such that the power of the pump light that is launched into the sensing fiber 24 simultaneously with the probe pulse is less than the power of the pump light launched in the sensing fiber 24 at other times (or at least one other time). The effect of this is that the propagating probe pulse is exposed to less pump power and hence experiences less Raman gain than the backscattered light that the probe pulse produces and which is exposed to a larger amount of pump power as it propagates back along the fiber (because it overlaps with a later part of the pump intensity profile, which has a greater intensity/higher power than the part with which the forward propagating probe pulse overlaps). Adjustment of the pump power that overlaps the probe pulse relative to the pump power outside this time window thus allows different levels of Raman gain to be applied to the probe pulse and the backscatter.

In one embodiment, it is proposed that the pump power be reduced to zero during the launch of the probe pulse.

Figure 6:
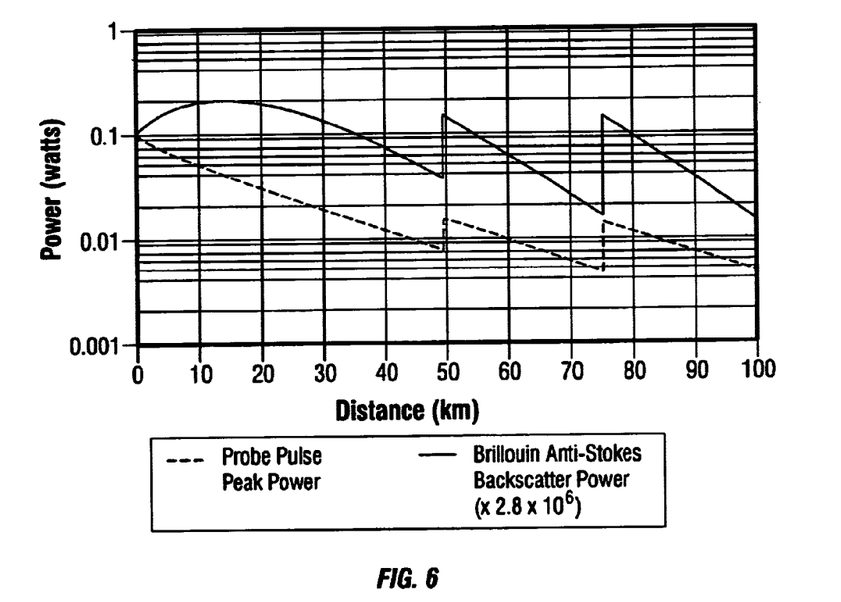
FIG. 6 shows plots of modelled intensities of Brillouin backscatter and of a probe pulse from the system of FIG. 5 used according to a first embodiment.

FIG. 6 shows the results of modelling the power of the backscatter (solid line) and the probe pulse (dashed line) under this condition. The pump power is eliminated during the launch of the probe pulse, the EDFA at 50 km has a gain of ×2 and the EDFA at 75 km has a gain of ×3, and the probe pulse power has been increased to 100 mW. The probe power can be raised in this way because the absence of simultaneous pump power and corresponding Raman amplification means that there is no risk that the probe power will be amplified to above the threshold for nonlinear effects. The greater probe power produces a greater backscatter power, which is then amplified. The overall effect is therefore to improve the backscatter signal while avoiding nonlinear distortion of the probe pulse. Note that the lowest backscatter power is higher than the lowest backscatter power for the system of FIG. 1, shown in FIG. 4, although the far end performance is reduced somewhat. Hence, the technique of removing pump power during the launch of the probe pulse allows performance to be improved at the near end of the sensing fiber, so this approach is useful for relatively short sensing fibers. Moreover, if a longer sensing fiber is required, the relative shortfall at the more remote parts of the fiber can be addressed by repositioning the remote EDFAs and/or increasing their gain.

Figure 7:
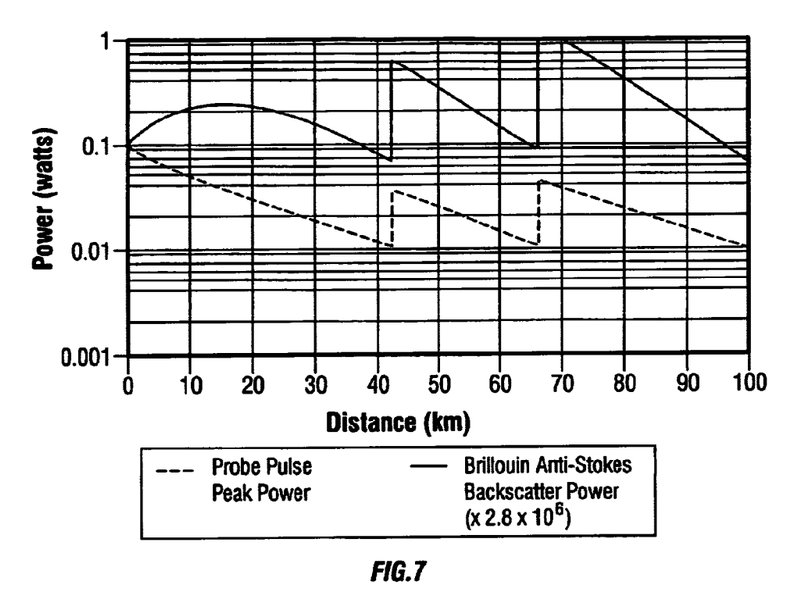
FIG. 7 shows plots of modelled intensities of Brillouin backscatter and of a probe pulse from the system of FIG. 5 used according to a second embodiment.

FIG. 7 shows the results of adjusting the EDFAs, again as a model of the backscatter power (solid line) and the probe power (dashed line). Here the pump power is turned off during the launching of the probe pulse and the probe pulse power is 100 mW. The amplifiers are moved to 42 km and 66 km and their gain is increased to ×3 and ×4 respectively. Comparison with FIG. 6 shows how this improves the far end performance, giving greatly increased backscatter power from this part of the fiber. The power is higher than for the prior art system modelled in FIG. 4 over most parts of the fiber.

Further optimisation of the EDFA gain and position is clearly possible. However, an alternative approach is to allow some limited Raman amplification of the probe pulse to occur, by reducing, rather than fully suppressing, the pump power that overlaps with the probe pulse on launch. Therefore, a further embodiment of the invention proposes that the pump power be non-zero during the launching of the probe pulse, but at a lower level than outside the window of the probe pulse. For this, it is important to consider the maximum value that the probe pulse power is allowed to reach, anywhere along the fiber. The precise maximum value is not essential, what is important is that some limit exists at which point nonlinear effects distort the measurement, so that the probe pulse power should preferably be kept below this limit, and not amplified above it by the Raman amplification supplied by the pump power. Consequently, the probe pulse power at launch will have to be less than this maximum level, to allow for the amplification. For the sake of the modelling used to illustrate the present invention, the maximum probe power value is taken to be 100 mW.

Figure 8:
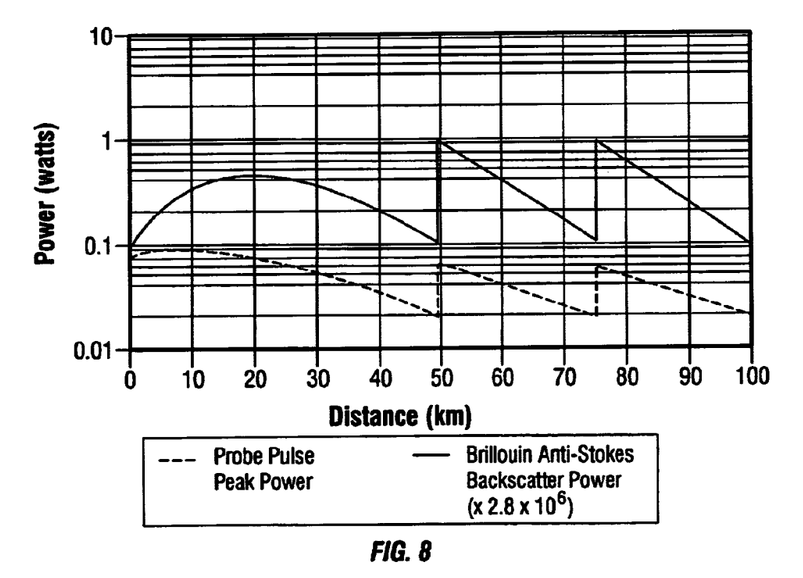
FIG. 8 shows plots of modelled intensities of Brillouin backscatter and of a probe pulse from the system of FIG. 5 used according to a third embodiment.

FIG. 8 shows the results of modelling the backscatter power (solid line) and the probe pulse power (dashed line) under such conditions. In this example, the pump power is reduced to 0.2 W during the launching of the probe pulse (and 0.4 W at other times, consistent with the model of the prior art system), and the probe pulse power is 80 mW. The amplifiers are at 50 km and 75 km and their gain is ×2 and ×3 respectively (again, this is consistent with the model of the prior art system, to allow comparison).

It can be seen from FIG. 8 that a small amount of Raman gain on the probe pulse delays the point at which the maximum power is reached for both the backscatter and the probe pulse (compared to the zero pump power arrangement of FIG. 7). The performance is now superior to the prior art system (FIG. 4) at all points along the fiber and, crucially, at the far end. This is achieved with no modification to the sensing fiber, only to the circuitry that controls the pump source. Hence the improvement offered by the present invention is easy to achieve, and can be implemented for existing sensing fibers with no need to de-install a fiber from its sensing location.

The invention also proposes to use shifting of the relative timing of the probe pulse and the pump intensity profile to control the gain available for the probe pulse over its propagation time. This can be achieved using a device that shifts the relative timing of the probe pulse with respect to the pump at some point along the fiber.

Figure 9:
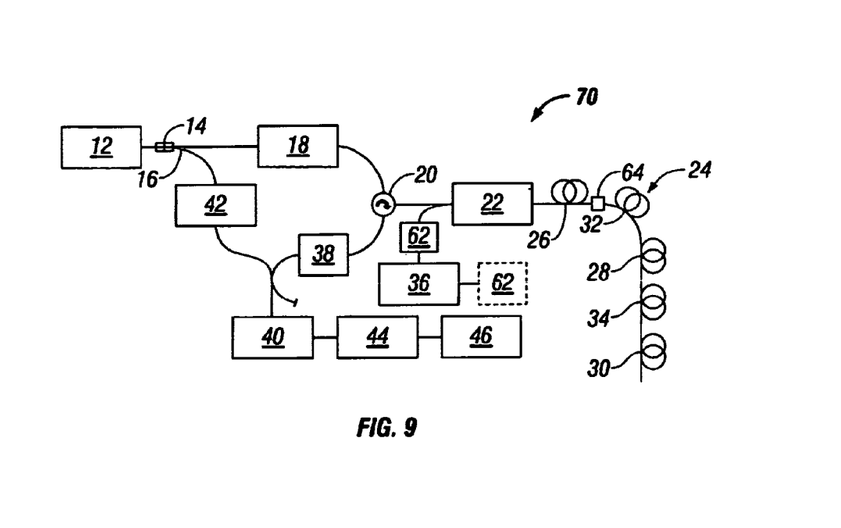
FIG. 9 shows a schematic diagram of an optical time domain reflectometer system according to a further embodiment of the present invention.

FIG. 9 shows a schematic diagram of an optical fiber sensing system that incorporates such a device. The system 70 includes the same features as the system 60 in FIG. 5, and additionally includes a time delay device 64 for introducing a delay into the time of one of the pump light or the probe pulse relative to the other. The device 64 is incorporated into the first length 26 of the sensing fiber 24 in this example. In other examples, the device may be incorporated further along the sensing fiber 24, after the first or second EDFA 32, 34, and/or more than one device may be included. Any optical delay device capable of introducing a relative time delay between two co-propagating wavelengths can be used.

Figure 10:
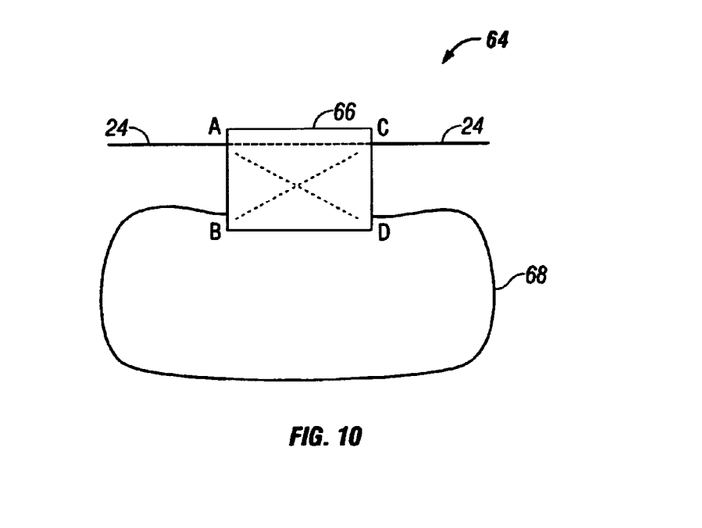
FIG. 10 shows a schematic diagram of an example fiber delay line that may be utilised with the system of FIG. 9.

FIG. 10 shows a schematic diagram of an example of a suitable optical time delay device 64, which is coupled into an optical sensing fiber 24. In this example, the optical time delay device 64 comprises a wavelength-division multiplexer (WDM) 66 and a fiber loop 68. The WDM 66 has four ports A-D comprising two upstream ports A and B and two downstream ports C and D. The sensing fiber 24 is connected to an upstream port A and a downstream port C, and the fiber loop 68 is coupled to the other upstream port B and the other downstream port D. The WDM 66 provides wavelength dependent cross-coupling between the upstream and downstream ports. In operation, light propagating along the sensing fiber 24 at both the probe wavelength and the pump wavelength enters the WDM 66 at upstream port A. One of the wavelengths travels straight through the WDM 66 to downstream port C and re-joins the sensing fiber 24. Meanwhile, the other wavelength crosses to the other downstream port D and enters the fiber loop 68. After propagating along the fiber loop 68, this light re-enters the WDM at the second upstream port B, and is directed to downstream port C to which the sensing fiber is coupled, so that the light is re-directed into the sensing fiber 24. At the point of re-entry to the sensing fiber 24, the light that has been around the fiber loop 68 is delayed in time with respect to the light that has been coupled directly through the WDM 66, owing to the extra distance it has travelled. The length of the fiber loop 68, or delay line, determines the relative delay between the wavelengths. Either of the pump or the probe wavelengths can be subjected to the delay.

Using such a device, the probe pulse can be shifted relative to the pump intensity profile so that the probe pulse then overlaps a different part of the pump power. In the case of a zero pump power at probe launch, this can be used to provide overlapping pump power for amplification of the probe pulse at a point downstream when the probe power has been depleted by propagation losses (including transfer to backscatter power) to a level at which it can safely be amplified without risk of nonlinear distortion. For non-zero pump power at probe launch, the pump pulse can be shifted to a new part of the pump profile once the initial overlapping lower pump power has been depleted by amplification of the probe pulse and propagation losses to a level where it no longer amplifies the probe pulse. Hence, the loss of power from the pump to the probe can be made up for by taking power from a different time slice of the pump power. This can delay the reduction of the pump power and thus of the amplification of the probe pulse. Moreover, because the location along the sensing fiber where this increase in pump power for the probe occurs is remote from the launch end and can be selected, it can have benefits including that it can be positioned when the probe power is sufficiently reduced relative to the maximum allowable probe power, the pump power used up in the amplification of the probe is in effect replenished, and it can exchange power with a time slice of the pump when the latter is back to full power, after allowing the probe pulse gain for the initial section of sensing fiber to be reduced.

Figure 11:
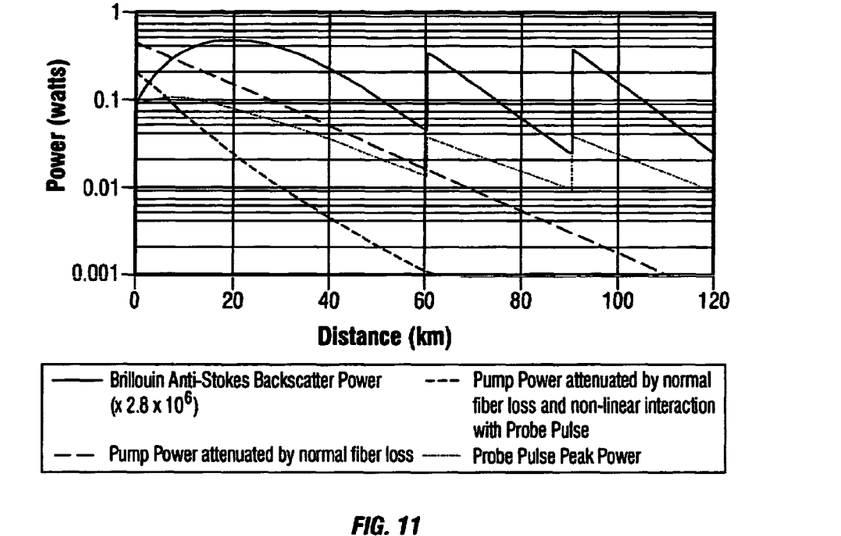
FIG. 11 shows plots of modelled intensities of Brillouin backscatter, of a probe pulse and of propagating pump power from the system of FIG. 5 used according to another embodiment.

To illustrate the effect of this time delay, first consider FIG. 11, which plots the backscatter power (solid line) and the probe pulse power (dot-dash line) for a system with EDFAs at 60 km and 90 km, and a non-zero pump power for probe launch, so that the probe pulse undergoes some initial amplification until the pump power becomes too depleted. Included in FIG. 11 are two additional curves. The long-dash line shows the pump power launched into the fiber, including the effects of attenuation, and shows that the power decreases with distance along the fiber, and the short-dash line shows the pump power travelling with the probe pulse. This line has a much steeper slope that the long-dash line, indicating that the pump power overlapping the probe pulse is depleted by transfer to the probe pulse by Raman amplification, in addition to attenuation.

Figure 12:
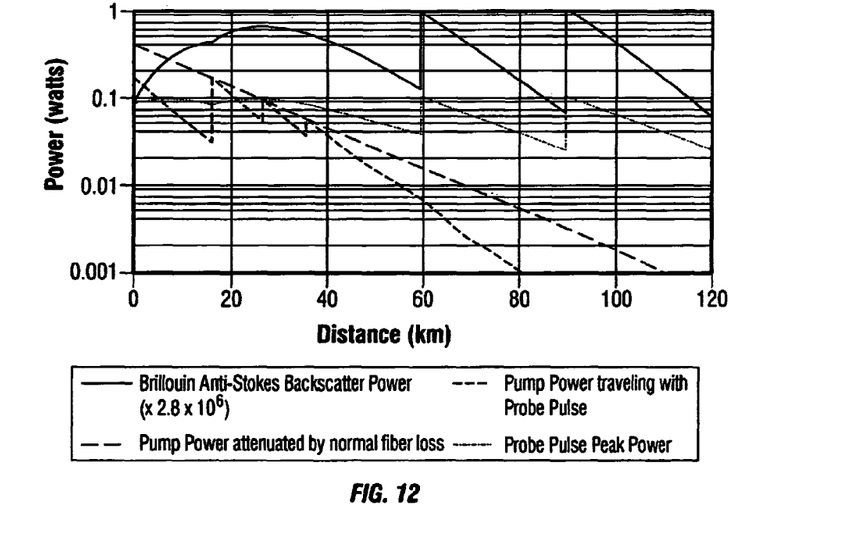
FIG. 12 shows plots of modelled intensities of Brillouin backscatter, of a probe pulse and of propagating pump power to show the effect of modifying the system of FIG. 5 in accordance with FIG. 9.

FIG. 12 plots the equivalent curves for a system that includes optical delay devices at 13.5 km, 27 km, and 36 km (i.e. three delay devices 64 all located in the first length 26 of the sensing fiber 24, before the first EDFA 32). These devices boost the pump power that overlaps with the probe pulse three times, as indicated by the three step increases in the pump power travelling with the probe pulse (short-dash line). Under these conditions, it can be seen that the probe power (dot-dash line) is able to remain at close to the maximum permitted level (100 mW, for this modelling) over a long distance (about 40 km) before the reduction in pump power is such that amplification of the probe pulse by the Raman effect can no longer continue. The solid line indicates the corresponding increase in the backscatter power.

The technique can be used more widely if higher pump power is available. For example, if the pump power is increased to 600 mW, and the WDM devices and amplifiers are re-positioned to 19.5 km, 30 km, 45 km, 66 km, and 99 km respectively, further improvement is achieved.

Figure 13:
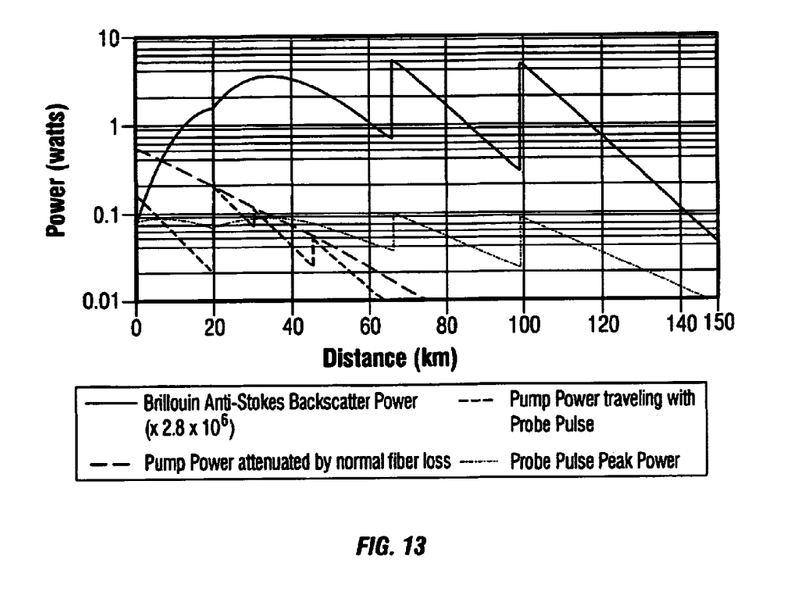
FIG. 13 shows further plots of modelled intensities of Brillouin backscatter, of a probe pulse and of propagating pump power to show the effect of modifying the system of FIG. 5 in accordance with FIG. 9.

FIG. 13 illustrates this, where the backscatter power, probe pulse power, overlapping pump power, and pump launch power are again shown as a solid line, a dot-dash line, a short-dash line, and a long-dash line. Now the backscatter signal is above the level which is known to give good performance over the entire fiber to 100 km and in fact only falls to the signal level of the prior art (FIG. 4) at around 150 km. This represents an increase in the range of the system of 50 km over the prior art system [1].

There are of course many ways in which the parameters of an optical fiber sensing system can be adjusted in accordance with the invention in order to optimise not only the range and the signal-to-noise ratio along the entire fiber, but also to minimise non-linearity, and also to reduce the dynamic range of the signals that need to be acquired. The probe pulse power and the pump power profile can be varied, and the quantity and position of any time-delay devices can be altered, as can the quantity, position, and gain of any fiber amplifiers. However, the principles of operation remain the same. Co-propagating pump light with the probe pulse within a sensing fiber is used to amplify at least the returning backscattered light and its power profile is modulated so that the pump power travelling with the probe pulse is different from the pump power that is used to amplify the returning backscatter signals. In addition, one or more devices may be arranged along the sensing fiber to vary the delay between the probe and the pump, so as to increase the Raman gain for the probe pulse further along the fiber without having to rely on chromatic dispersion (different wavelengths having different velocities inside the fiber) to bring the probe pulse into overlap with a certain part of the pump profile. Also, one or more discrete rare-earth doped fiber amplifiers may be incorporated into the sensing fiber. Furthermore, it is also possible to add additional fibers specifically to couple pump power into the sensing fiber at specific locations; this is another approach for altering the overlap between the probe pulse and the pump power profile downstream of the coupling location, to modify the amount of Raman amplification available for the probe pulse.

The particular optical fiber sensing systems shown in FIGS. 5 and 9 are illustrative examples only, and the invention is not so limited. As indicated in the preceding paragraph, the optical powers and the locations of the components along the sensing fiber can be varied as desired. Other optical sources, detection arrangements, and processing apparatus can be employed. Also, the various embodiments of the invention are applicable to a wide range of fiber sensing systems, such as optical time domain resolution systems including those that measure Rayleigh, Brillouin, and/or Raman backscatter. The invention is particularly beneficial in systems where the optical bandwidth of the backscatter is narrow (such as coherent Rayleigh and Brillouin-based systems), because the Raman amplification will be more constant across the bandwidth. Other fiber systems can also exploit the invention, such as systems that measure attenuation (loss), and systems that are used to interrogate various types of discrete optical sensor using a time-domain approach.

REFERENCES

[1] Cho, Y.-T., et al. 100 *km Distributed Fiber Optic Sensor Based on the Coherent Detection of Brillouin Backscatter, with a Spatial Resolution of* 10 *m, Enhanced Using Two Stages of Remotely Pumped Erbium-Doped Fiber Combined with Raman Amplification*. Proceedings Submitted to 18th Conference on Optical Fiber Sensing. 2006. Cancun, Mexico.

[2] Alahbabi, M. N., Y.-T. Cho and T. P. Newson, 150-*km-range distributed temperature sensor based on coherent detection of spontaneous Brillouin backscatter and in-line Raman amplification*. Journal of the Optical Society of America B, 2005. 22(6): p. 1321-1324.

[3] Cho, Y.-T., et al., *Enhanced performance of long range Brillouin intensity based temperature sensors using remote Raman amplification*. Measurement Science & Technology, 2004. 15(8): p. 1548-1552.

[4] WO 03/065619

[5] Kee, H. H., G. P. Lees and T. P. Newson, *Extended-range optical time domain reflectometry system at* 1.65 μ*m based on delayed Raman amplification*. Optics Letters, 1998. 23(5): p. 349-351.

[6] Cho, Y.-T., et al., 50-*km single-ended spontaneous-Brillouin-based distributed-temperature sensor exploiting pulsed Raman amplification*. Optics Letters, 2003. 28(18): p. 1651-1653.

What is claimed is:

1. A method of providing Raman amplification in an optical fiber sensing system, comprising:
    generating a probe pulse of light at a probe wavelength;
    launching the probe pulse into a sensing optical fiber;
    generating pump light at a pump wavelength shorter than the probe wavelength;
    modulating the pump light to produce a time-varying intensity profile;
    launching the modulated pump light into the sensing fiber such that the intensity of the launched modulated pump light during launch of the probe pulse is different from the intensity of the launched modulated pump light at one or more other times; and
    propagating the launched modulated pump light and the probe pulse along the sensing fiber to control Raman amplification of backscattered light produced by the probe pulse separately from Raman amplification of the probe pulse.

2. A method according to claim 1, wherein the intensity of the launched modulated pump light during launch of the probe pulse is substantially zero so that the probe pulse experiences substantially no Raman amplification.

3. A method according to claim 1, wherein the intensity of the launched modulated pump light during launch of the probe pulse is greater than zero so that the probe pulse experiences Raman amplification.

4. A method according to claim 3, wherein the intensity of the launched modulated pump light during the launch of the probe pulse is sufficient to amplify the probe pulse to an intensity below a threshold above which the probe pulse would be distorted by nonlinear effects.

5. A method according to claim 1, and further comprising introducing, at a location along the sensing fiber, a time delay into forward propagating light at either the probe wavelength or the pump wavelength sufficient to overlap the probe pulse with a part of the intensity profile of the launched modulated pump light having a greater intensity than the part overlapped by the probe pulse before the location along the fiber.

6. A method according to claim 5, wherein, during the overlap, the probe pulse is amplified by the pump light to an intensity below a threshold above which the probe pulse would be distorted by nonlinear effects.

7. A method according to claim 1, and further comprising passing forward propagating light in the sensing fiber through one or more rare earth-doped optical fiber amplifiers integrated into the sensing fiber to amplify the intensity of the light.

8. A method according to claim 1, and further comprising:
    collecting backscattered light returned from the sensing fiber; and
    processing the collected backscattered light to determine information about the sensing fiber and/or an environment in which it is deployed.

9. An optical fiber sensing system for providing Raman amplification, comprising:
    a sensing optical fiber deployable in a sensing environment;

a first optical source operable to generate probe pulses of light at a probe wavelength;

a second optical source operable to generate pump light at a pump wavelength shorter than the probe wavelength;

means operable to modulate the pump light generated by the second optical source to produce a time-varying intensity profile; and an optical coupling device arranged to receive the probe pulses from the first optical source and modulated pump light from the modulation means and to launch the probe pulses and the modulated pump light into the sensing fiber for propagation along the sensing fiber to control Raman amplification of backscattered light produced by the probe pulses separately from Raman amplification of the probe pulses.

10. An optical fiber sensing system according to claim 9, in which the intensity of the launched modulated pump light during launch of the probe pulse is substantially zero so that the probe pulse experiences substantially no Raman amplification.

11. An optical fiber sensing system according to claim 9, in which the intensity of the launched modulated pump light during launch of the probe pulse is greater than zero so that the probe pulse experiences some Raman amplification.

12. An optical fiber sensing system according to claim 11, in which the intensity of the launched modulated pump light during the launch of the probe pulse is sufficient to amplify the probe pulse to an intensity below a threshold above which the probe pulse would be distorted by nonlinear effects.

13. An optical fiber sensing system according to claim 9, and further comprising an optical time delay device integrated into the sensing fiber and operable to introduce a time delay into forward propagating light in the sensing fiber at either the probe wavelength or the pump wavelength such that after the delay, the probe pulse overlaps a part of the intensity profile of the pump light having a greater intensity than the part overlapped by the probe pulse before the delay, and experiences Raman amplification.

14. An optical fiber sensing system according to claim 13, in which the optical time delay device is located such that the intensities of the probe pulse and of the pump light with which it overlaps after the delay are such that the probe pulse is amplified by the pump light to an intensity below a threshold above which the probe pulse would be distorted by nonlinear effects.

15. An optical fiber sensing system according to claim 13, in which the optical time delay device comprises an optical fiber delay line coupled at both ends to the sensing fiber by a wavelength division multiplexer arrangement configured to pass light at one of the pump wavelength and the probe wavelength directly along the sensing fiber and to direct light at the other of the pump wavelength and the probe wavelength along the optical delay line before directing it further along the sensing fiber.

16. An optical fiber sensing system according to claim 9, and further comprising one or more rare-earth optical fiber amplifiers integrated into the sensing fiber and operable to amplify the intensity of forward propagating light in the sensing fiber.

17. An optical fiber sensing system according to claim 9, and further comprising:

an optical detector for collecting backscattered light returned from the sensing fiber; and a processor operable to process one or more signals output from the optical detector to determine information about the sensing fiber and/or an environment in which it is deployed.

18. A method comprising:

launching a probe pulse of light into a sensing optical fiber;

launching pump light into the sensing optical fiber, the pump light having a time-varying intensity profile; and propagating the pump light along the sensing fiber relative to the probe pulse such that Raman amplification by the pump light of the probe pulse is controlled separately from Raman amplification of backscattered light produced in response to the probe pulse.

19. The method according to claim 18, wherein controlling propagation comprises propagating pump light having a first intensity during the propagation of the probe pulse, and propagating pump light having a second intensity at a time other than during launching of the probe pulse, wherein the first intensity is different than the second intensity.

20. The method according to claim 19, wherein the first intensity does not produce Raman amplification of the probe pulse.

21. The method according to claim 18, wherein controlling propagation comprises delaying, at a location along the sensing optical fiber, forward propagating light at either a wavelength of the probe pulse of light or a wavelength of the pump light for a time sufficient to overlap the probe pulse with a portion of the pump light having a greater intensity than the portion of the pump light overlapped by the probe pulse prior to the location along the sensing optical fiber.

\* \* \* \* \*